United States Patent
Lestage et al.

(10) Patent No.: US 8,354,364 B2
(45) Date of Patent: Jan. 15, 2013

(54) FOAMABLE COMPOSITION CONTAINING ALCOHOL

(75) Inventors: David Lestage, Livermore, CA (US); David R. Scheuing, Danville, CA (US); Scott L. Cumberland, Pleasanton, CA (US); Grant Templin, Dublin, CA (US)

(73) Assignee: The Clorox Company, Oakland, CA (US)

( * ) Notice: Subject to any disclaimer, the term of this patent is extended or adjusted under 35 U.S.C. 154(b) by 446 days.

(21) Appl. No.: 12/753,498

(22) Filed: Apr. 2, 2010

(65) Prior Publication Data

US 2010/0189611 A1 Jul. 29, 2010

Related U.S. Application Data

(62) Division of application No. 11/466,657, filed on Aug. 23, 2006, now Pat. No. 7,723,279.

(51) Int. Cl.
*C11D 1/00* (2006.01)

(52) U.S. Cl. ........ 510/138; 510/119; 510/156; 510/479; 510/506

(58) Field of Classification Search .......... None
See application file for complete search history.

(56) References Cited

U.S. PATENT DOCUMENTS

| | | | |
|---|---|---|---|
| 3,131,153 A | 4/1964 | Klausner | |
| 3,962,150 A | 6/1976 | Viola | |
| 4,915,934 A | 4/1990 | Tomlinson | |
| 4,981,677 A | 1/1991 | Thau | |
| 5,167,950 A | 12/1992 | Lins | |
| 5,888,478 A | 3/1999 | Maurin | |
| 6,082,586 A | 7/2000 | Banks | |
| 6,299,862 B1 | 10/2001 | Barrow | |
| 6,333,039 B1 | 12/2001 | Fendler et al. | |
| 6,383,651 B1 | 5/2002 | Weinert et al. | |
| 6,403,760 B1 | 6/2002 | Weinert et al. | |
| 6,465,565 B1 | 10/2002 | Garcia et al. | |
| 6,465,566 B2 | 10/2002 | Garcia et al. | |
| 6,495,636 B2 | 12/2002 | Sugiyama et al. | |
| 6,518,229 B2 | 2/2003 | Tashjian | |
| 6,660,828 B2 | 12/2003 | Thomas et al. | |
| 6,727,344 B2 | 4/2004 | Weinert et al. | |
| 2003/0060571 A1 | 3/2003 | Weinert et al. | |
| 2003/0109662 A1 | 6/2003 | Medsker et al. | |
| 2003/0149186 A1 | 8/2003 | Medsker et al. | |
| 2004/0131578 A1 | 7/2004 | Geria | |
| 2005/0129626 A1 | 6/2005 | Koivisto et al. | |
| 2006/0104911 A1* | 5/2006 | Novak | 424/45 |
| 2006/0104919 A1 | 5/2006 | Novak | |
| 2006/0281663 A1 | 12/2006 | Asmus | |

FOREIGN PATENT DOCUMENTS

| | | |
|---|---|---|
| EP | 0792632 | 5/1998 |
| EP | 9057898 | 10/2003 |
| WO | WO 02/92660 | 5/2002 |
| WO | WO 03/093568 | 4/2003 |
| WO | WO 03/051959 | 6/2003 |
| WO | WO 2004/053006 | 6/2004 |
| WO | WO 2006/006688 | 6/2006 |

OTHER PUBLICATIONS

Food and Drug Administration. Topical Antimicrobial Products . . . Over-the-Counter Use . . . Antiseptic Drug Products,: Federal Register, 1994; 59:31221-2.
Martin, J.W. et al, "Dietary Accumulation of Perfluorinated Acids in Juvenile Rainbow Trout," Environ. Toxicol. Chem., 2003, 22, 189.
Martin, J.W. et al., "Bioconcentration and Tissue Distribution of Perfluorinated Acids in Rainbow Trout," Environ. Toxicol. Chem., 2003, 22, 196.
Omnova Solutions, Inc., "Fluorosurfactants for Improved Flow, Leveling and Surface Appearance in Aqueous Coatings," Mar. 7, 2006.
"Clean Hands Save Lives," Source: Coordinating Center for Infectious Diseases; [online], May 11, 2006 [retrieved Aug. 22, 2006] http://www.cdc.gov/cleanhands/.
Perfluoroctanoic acid (PFOA);: Source: Environmental Protection Agency (EPA), [online]. dated: uknown [retrieved Aug. 22, 2005]. http://www.epa.gov.oppt.pfoa/.
U.S. Appl. No. 11/105,819, filed Apr. 14, 2005, assigned to The Clorox Company.

\* cited by examiner

*Primary Examiner* — Necholus Ogden, Jr.
(74) *Attorney, Agent, or Firm* — Erin Collins

(57) ABSTRACT

This invention relates to compositions containing lower (C1-C4) alcohol and a polymeric fluorosurfactant formulated for being dispensed as a foam product. More particularly, the invention relates to improved compositions formulated with polymeric fluorosurfactants with pendant perfluoroalkyl side chains of a fully fluorinated chain length of C1-C7. The compositions also relate to use for personal care, such as skin sanitizing and cleansing.

16 Claims, No Drawings

FOAMABLE COMPOSITION CONTAINING ALCOHOL

This application is a divisional application of U.S. patent application entitled "Foamable Composition Containing Alcohol" and having Ser. No. 11/466,657, which was filed on Aug. 23, 2006, now U.S. Pat. No. 7,723,279B2.

FIELD OF THE INVENTION

This invention relates to compositions containing a lower alcohol, having from one to four carbon atoms, and a polymeric fluorosurfactant formulated for being dispensed as a foam product and, more particularly, to improved compositions capable of being dispensed as a foam product for use as a hand cleanser or sanitizer. The compositions are constructed with fluorosurfactants derived from fluorinated oxetanes.

BACKGROUND OF THE INVENTION

The Center for Disease Control recommends "[k]eeping hands clean is one of the most important steps we can take to avoid getting sick and spreading germs to others. It is best to wash your hands with soap and clean running water for 20 seconds. However, if soap and clean water are not available, use an alcohol-based product to clean your hands. Alcohol-based hand rubs significantly reduce the number of germs on skin and are fast acting". ("Clean Hands Save Lives"; Source: Coordinating Center for Infectious Diseases"; [online], Dated: May 11, 2006, [retrieved on Aug. 22, 2006]. Retrieved from the internet: <URL: http://www.cdc.gov/cleanhands/>.)

Washing with soap and water is not always available or convenient. Adults often don't have time to wash thoroughly and children often don't do a complete job due to inexperience or distraction. Thus, many people use hand sanitizers in the absence of soap and water.

For alcohol based hand sanitizers, the Food and Drug Administration (FDA) recommends a concentration of 60% to 95% ethanol, the concentration range of greatest germicidal efficacy. (Food and Drug Administration. Topical antimicrobial products for over-the-counter use; tentative final monograph for healthcare antiseptic drug products. Federal Register. 1994; 59:31221-2.)

In the past, lower alcohols (C1-C4), such as ethanol, were considered to be de-foamers rather than foam promoting compounds. U.S. Pat. No. 3,131,153 to Klausner, herein incorporated by reference, describes that in foam producing compositions using propellants, decreasing amounts of alcohol in the formulation favors a more stable foam. If the amounts of alcohol are outside the indicated critical ranges of 26-64%, emulsification will result, rather than a homogeneous composition. U.S. Pat. No. 3,962,150A to Viola, herein incorporated by reference, describes foam-producing skin cleansing compositions suitable for use in a non-pressurized system, including a total surfactant composition of from 1 to 15% and from 1.0 to 15.0% of an alcoholic solvent having from 2 to 3 carbon atoms and from 70 to 98% by weight of water. U.S. Pat. No. 6,518,229B2 to Tashjian et al, herein incorporated by reference, describes a non-alcohol foaming antibacterial soap composition which includes an anionic surfactant, an amphoteric surfactant, a cationic conditioning agent, an antibacterial agent, such as Triclosan®, and water. To obtain a high level of foam, an amphoteric surfactant is used to function as a foam booster.

Various examples of foaming lower alcohol (C1-C4) compositions comprised of a high content of alcohol have been described. U.S. Pat. No. 5,167,950 to Lins, herein incorporated by reference, describes an antimicrobial aerosol mousse having a high alcohol content of at least 52%.

US20050129626 to Koivisto et al and US20060104919 to Novak, both of which are herein incorporated by reference, describe foaming a high alcohol content composition including a lower alcohol and perfluorinated surfactants. Perfluorinated surfactants are synthetic chemicals that do not occur naturally in the environment. Perfluorinated surfactants are sometimes referred to as "C8", because a typical structure has a linear chain of eight fluorinated carbon atoms. Perfluorinated surfactants are sometimes employed in the production of fluoropolymers, substances with special properties that have thousands of important manufacturing and industrial applications.

Commonly used perfluorinated surfactants and their derivates include perfluoroalkyl phosphate salt, perfluoroalkyl phosphate compounds, fluoroaliphatic phosphate esters, fluoroaliphatic amine oxides, polytetrafluoroethylene acetoxypropyl betaine, anionic phosphate fluorosurfactant and mixtures thereof. Perfluorinated surfactants can also include ethoxylates, glycerol esters, amine oxides, acetylenic alcohol derivatives, carboxylates, phosphates, carbohydrate derivatives, sulfonates, betaines, esters, polyamides, silicones, and hydrocarbon surfactants that have been fluorinated. Accordingly, the use of these surfactants are described in US 20060104919A1 to Novak and US 20050129626 to Koivisto et al.

In 1999, the EPA became interested in perfluorinated compounds after receiving data on perfluorooctyl sulfonate (PFOS). Data showed that PFOS was persistent, unexpectedly toxic, bioaccumulative, and found in very low concentrations in the blood of the general population and in wildlife around the world. In general, the durability of perfluorinated compounds prevent them from breaking down once in the environment and this results in the buildup and bioaccumulation in the environment. ("Perfluorooctanoic acid (PFOA)"; Source: Environmental Protection Agency (EPA).) [online], dated: unknown, [retrieved on Aug. 22, 2006]. Retrieved from the internet: <URL:http://www.epa.gov/oppt/pfoa/>.)

On Feb. 15, 2006, the EPA's Science Advisory Board voted to approve a recommendation that certain perfluorinated surfactants should be considered as likely carcinogenic.

The fluorosurfactants used in the present invention are polymeric fluorosurfactants with pendant perfluoroalkyl side chains of a fully fluorinated chain length of C1-C7 and are not known to bioaccumulate. Furthermore, the polymeric fluorosurfactants of the present invention are surprisingly and unexpectedly useful to foam formulations containing a lower alcohol and water. Accordingly, it has been known in the art that such polymeric fluorosurfactants exhibit very low foaming characteristics. (Omnova Solutions Inc., "Fluorosurfactants for Improved Flow, Leveling and Surface Appearance in Aqueous Coatings", Mar. 7, 2006.)

The invention overcomes the shortcomings of past compositions by providing a foaming composition, which includes a lower alcohol but does not use a fluorosurfactant known to bioaccumulate in the environment.

SUMMARY OF THE INVENTION

The present invention provides novel compositions for foaming lower alcohol content formulations, which include polymeric fluorosurfactants with pendant perfluoroalkyl side chains of a fully fluorinated chain length of C1-C7.

The present invention also provides a novel composition for foaming high alcohol content formulations, containing a C1-C4 alcohol and mixtures thereof.

The present invention also provides a novel foaming composition which can be used in an un-pressurized system and without propellants.

The present invention also provides a novel foaming composition effective to sanitize a surface, such as human or animal skin or hands.

The present invention also provides a delivery system for treating a surface. The delivery system includes a polymeric fluorosurfactant and a dispensing device capable of foaming the composition.

The present invention further relates to methods for using the compositions to clean or sanitize a surface, such as human or animal skin or hands.

These and other aspects will become readily apparent from the detailed description which follows.

DETAILED DESCRIPTION OF THE INVENTION

The compositions of the present invention can comprise, consist of or consist essentially of the essential elements and limitations of the invention described herein, as well as any of the additional or optional ingredients, components, or limitations described herein.

Before describing the present invention in detail, it is to be understood that this invention is not limited to particularly exemplified compositions, methods or kits that may, of course, vary. It is also to be understood that the terminology used herein is for the purpose of describing particular embodiments of the invention only, and is not intended to limit the spirit and scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

In the application, effective amounts are generally those amounts listed as the ranges or levels of ingredients in the descriptions, which follow hereto. Unless otherwise stated, amounts listed in percentage ("%'s") are in weight percent (based on 100% active) of the composition alone.

DEFINITIONS

"Antibacterial agent" or "Antimicrobial agent" as used herein includes agents capable of killing, inhibiting or reducing the growth of any of a broad spectrum of pathogenic microorganisms such as bacteria, yeast, fungi, algae, viruses, and mold.

"Detergent" as used herein means a compound, or a combination of compounds, that is put to use for example, cleaning purposes or stabilizing the formula. A detergent can be a surfactant.

"Emollient" as used herein means a compound added to increase the moisture content on a surface.

"Emulsifier" as used herein is synonymous with "surfactant" and refers to molecules which may stabilize an emulsion. An emulsifier may be a foam booster.

"Fluorinated", as used herein means a molecule containing at least one fluorine atom.

"Foam Booster" as used herein means a compound capable of enhancing foamability or stability of the composition. A foam booster may be an emulsifier.

"Instant Sanitizing" as used herein means the compositions of the present invention are capable of sanitizing without the need for soap and water.

"Perfluorinated" as used herein means a compound or radical in which all hydrogen atoms, except those whose replacement would affect the nature or characteristic groups present, have been replaced by a fluorine atom. An example of a perfluorinated surfactant is perfluorooctanoic acid (PFOA), also known as C8, and has the formula $C_8HF_{15}O_2$. The chemical structure is

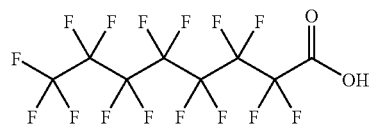 [SMILES: O=C(O)C(F)(F)C(F)(F)C(F)(F)C(F)(F)C(F)(F)C(F)(F)C(F)(F)F]

Another example of perfluorinated surfactant is perfluorooctane sulfonate (PFOS), the conjugate base of perfluorooctane sulfonic acid, which has the formula $C_8F_{17}SO_3^-$. Salts of this anion are used as surfactants. The chemical structure is

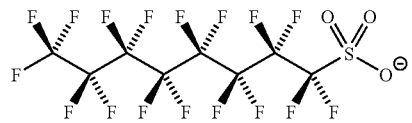

"Polymer" as used herein generally includes, but is not limited to, homopolymers, copolymers, such as for example, block, graft, random and alternating copolymers, terpolymers, and higher "x"mers, further including their derivatives, combinations, and blends thereof. Furthermore, unless otherwise specifically limited, the term "polymer" shall include all possible isomeric configurations of the molecule, including, but are not limited to isotactic, syndiotactic and random symmetries, and combinations thereof. Furthermore, unless otherwise specifically limited, the term "polymer" shall include all possible geometrical configurations of the molecule including, but not limited to linear, block, graft, random, alternating, branched and highly branched structures including comb, graft, starburst, dendrimers and dendrimeric structures thereof, and combinations.

"Sanitize" as used herein means that any of a broad spectrum of pathogenic microorganisms such as bacteria, yeast, fungi, algae, viruses, and mold is killed, inhibited or reduced.

"Surfactant" as used herein means a substance or compound that reduces surface tension when dissolved in a solvent or that reduces interfacial tension between two liquids, or between a liquid and a solid. Surfactant as used herein includes anionic, nonionic and amphoteric agents. A surfactant can be a detergent.

As used herein and in the claims, the term "comprising" is inclusive or open-ended and does not exclude additional unrecited elements, compositional components, or method steps. Accordingly, the term "comprising" encompasses the more restrictive terms "consisting essentially of" and "consisting of".

It must be noted that, as used in this specification and the appended claims, the singular forms "a," "an" and "the" include plural referents unless the content clearly dictates otherwise. Thus, for example, reference to a "surfactant" includes two or more such surfactants.

Unless defined otherwise, all technical and scientific terms used herein have the same meaning as commonly understood by one of ordinary skill in the art to which the invention pertains.

Fluorosurfactants

In the practice of this invention, the principal consideration in the selection of a suitable fluorosurfactant includes toxicity and the potential for bioaccumulation. Surprisingly and unexpectedly, Applicants have found that it is possible to foam C1-C4 alcohol content formulations using a novel group of polymeric fluorosurfactants with pendant perfluoroalkyl side chains of a fully fluorinated chain length of about C1-C7. More specifically, the pendant fluoro-side chain length is about C1-C4 and more specifically it is about C1-C2. Additionally, Applicants have found it possible to foam a high content of the C1-C4 alcohol in a formulation.

Without being bound by theory, it is believed that due to the pendant side chain the polymeric fluorosurfactants described herein are not readily biodegradable (generally less than 5% degradation after 28 days). This means that the fluorosurfactants are very stable and unlikely to degrade to any small molecule such as a carboxylic acid. The bioaccumulation and bioconcentration of perfluorocarboxylic acids have been studied. The results obtained by these studies show that perfluorocarboxylic acids with fully fluorinated chains of C4 and below do not bioaccumulate. (Martin, J. W.; Mabury, S. A.; Solomon, K. R.; Muir, D. C. G. Dietary Accumulation of Perfluorinated Acids in Juvenile Rainbow Trout. Environ. Toxicol. Chem., 2003, 22, 189. Martin, J. W.; and Mabury, S. A.; Solomon, K. R.; Muir, D. C. G. Bioconcentration and Tissue Distribution of Perfluorinated Acids in Rainbow Trout (Oncorhynchus mykiss). Environ. Toxicol. Chem., 2003, 22, 196.)

The polymeric fluorosurfactants used in the present invention include neutral, anionic, cationic, zwitterionic and ionizable partially fluorinated polymeric surfactants, and mixtures thereof. Partially fluorinated polymeric surfactants generally include those materials that are not fully perfluorinated, i.e. that contain non-fluorinated carbon centers and non-fluorinated alkyl groups. It is found that by employing partially fluorinated polymeric surfactants, foaming properties of the present invention are surprisingly good. Generally, partially fluorinated materials having perfluorinated alkyl substituents are from about C1-C7, more specifically, from C1-C4 and more specifically from C1-C2.

Examples of suitable polymeric fluorosurfactants include, but are not limited to, those materials corresponding to the general structures I-IV below:

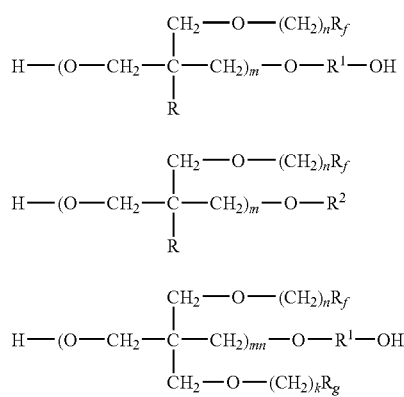

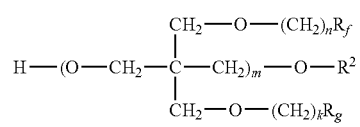

wherein m>1 to about 100, n is about 1 to about 50, k is about 1 to about 50 including n=k, wherein $R_f$ and $R_g$ are independently selected from perfluorinated alkyl radical, perfluorinated aryl radical, partially fluorinated alkyl radical, partially fluorinated aryl radical, derivatives thereof, combinations thereof, and R is hydrogen, or an alkyl comprising from 1 to 6 carbon atoms, $R^1$ is an alkyl having from 1 to 18 carbon atoms, $R^2$ is an alkyl having from 1 to 40 carbon atoms, wherein R, $R^1$ and $R^2$ may independently be alkyl and alkylene moieties derivatized with radicals selected from carboxylic, ester, amine, amide, aminoamide, siloxane, silyl, alkylsiloxane, perfluoroalkyl and combinations thereof.

Also suitable are derivatives of any one of the polymeric fluorosurfactants represented by formula I-IV herein above, in which derivation at any one or more alkyl positions is independently performed by covalent attachment of polar anionic groups, including for example, but not limited to carboxylate, alkyl esters, sulfate, sulfonate, phosphate, nitrate, and the like; covalent attachment of cationic groups, including for example, but not limited to ammonium, quaternary ammonium, quaternary alkyl ammonium, and the like; covalent attachment of polar nonionic groups, including for example, but not limited to poly(alkylene oxide), such as poly(ethylene oxide) and poly(propylene oxide), polyether copolymers, carbonyl, nitrile, thiol, and cyano groups, and combinations thereof.

Suitable examples of the polymeric fluorosurfactants useful in the present invention include those derived from polymerizing appropriate fluorinated oxetane monomers to obtain fluorosurfactants corresponding to any one of structures I-IV wherein $R_f$ and $R_g$ are selected from —$CF_3$, —$CF_2CF_3$, —$(CF_2)_pCF_3$, —R'$CF_3$, —R'$(CF_3)_p$, —R''$(CF_3)_q$, wherein R' is a C1 to C20 linear or branched, alkyl or alkylene moiety, optionally substituted with and terminated with at least one —$CF_3$ group, R'' is radical comprising a benzyl, phenyl, aryl group and combinations thereof with q degrees of —$CF_3$ substitution, wherein p is about 1 to about 10, and q is about 1 to about 5.

An example of commercially available polymeric fluorosurfactants include those corresponding to structures I-IV in which $R_f$ and $R_g$ correspond to —$(CF_2)_pCF_3$ with p=3, equivalent to —$CF_2$—$CF_2$—$CF_2$—$CF_3$ (—$C_4F_9$). There are other polymeric fluorosurfactants and derivatives suitable for use in the present invention are described in U.S. Pat. No. 6,403,760 to Weinert, et al., US20030060571 to Weinert, et al., US20030149186 to Medsker et al., U.S. Pat. No. 6,660, 828 to Thomas, et al., U.S. Pat. No. 6,403,760 to Weinert et al., and U.S. patent application Ser. No. 11/105,819, filed Apr. 14, 2005 to Applicant, which are all hereby incorporated by reference.

Other suitable examples of the polymeric fluorosurfactants useful in the present invention include those derived from structures I-IV by covalent attachment of polar anionic groups such as carboxylate, sulfate, sulfonate, phosphate, and nitrate. Useful counterions for these groups include $Li^+$, $Na^+$, $K^+$, $Cs^+$, and ammonium or alkyl ammonium groups. Also suitable are polymer derivatized polymeric fluorosurfactants described in US20030166785 to Medsker et al., and U.S. Pat. No. 6,383,651 to Weinert, et al., both of which are hereby incorporated by reference. Also suitable are copolymers with perfluorinated oxetane compounds formed via radical polymerization and cationic polymerizations such as those described in U.S. Pat. No. 6,495,636 to Sugiyama, et al., which is hereby incorporated by reference.

In addition, structure V is an example of a useful anionic polymeric fluorosurfactant that may be employed in the present invention.

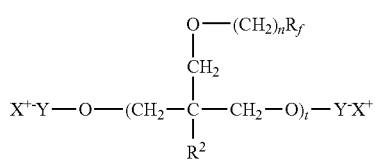

wherein t typically ranges from about 6 to about 8, but may be any value from 1 to about 100, n is about 1 to about 50, $R_f$ is selected from $-CF_3$, $-CF_2CF_3$, $-(CF_2)_pCF_3$, $-R'CF_3$, $-R'(CF_3)_p$, $-R''(CF_3)_q$, wherein R' is a C1 to C20 linear or branched, alkyl or alkylene moiety, optionally substituted with and terminated with at least one $-CF_3$ group, R'' is a radical comprising a benzyl, phenyl and aryl group with q degrees of $-CF_3$ substitution, wherein p is 1 to about 10, and q is between 1 and 5, $R^2$ is an alkyl having from 1 to 40 carbon atoms, further including alkyl and alkylene moieties derivatized with radicals selected from carboxylic, ester, amine, amide, aminoamide, siloxane, silyl, alkylsiloxane, perfluoroalkyl and/or combinations thereof, $X^+$ is any suitable cationic counterion as described herein, and wherein $Y^-$ is an anionic moiety selected from carbonate, borate, sulfate, sulfonate, phosphate, phosphonate, nitrate and/or combinations thereof. An example of a commercially available material corresponding to structure V is wherein n is about 1, $R_f$ is $-CF_2CF_3$, $R^2$ is $-CH_3$ and Y is $SO_3^-$, thus being a sulfate moiety and $X^+$ is $Na^+$ or $NH_4^+$.

Other suitable examples of polymeric fluorosurfactants useful in the present invention include those containing covalently bonded cationic groups such as ammonium or quaternary ammonium, or phosphonium. The anionic counterions associated with these groups can include fluoride, chloride, bromide, iodide, and tetrafluoroborate ($BF_4^-$). Other polymeric fluorosurfactants useful in the present invention include those containing covalently bonded polar nonionic groups. These nonionic groups may be selected from various polyethers having from about 1 to about 100 repeat units (n), and include, but are not limited to groups such as $-O-(CH_2CH_2O)_n-H$ (poly(ethylene oxide)), $-O-CH_2(CH_3)CH_2O)n-H$ (poly(propylene oxide)), polyether copolymers, carbonyl, nitrile, thiol, and/or cyano groups, and combinations thereof.

Still other polymeric fluorosurfactants useful in the present invention include those containing covalently bonded polar zwitterionic groups, forming an amphoteric type polymeric fluorosurfactant.

In the polymeric fluorosurfactants of the present invention, the polar group or groups may be covalently bonded to the ends of the polymeric fluorosurfactant. Also suitable, however, are polymeric fluorosurfactants in which the polar groups, or additional non-terminally bonded polar groups, are also covalently bonded at other positions on the polymeric fluorosurfactant molecule. Any variety of synthetic schemes may be used to attach the polar groups to polymeric fluorosurfactants suitable for use, including addition through polymerization with initiators or chain transfer agents, grafting reactions, addition reactions such as condensation of a hydroxyl group with an isocyanate that contains a polar group to be added, substitution or metathesis, or esterification of a hydroxyl group with sulfuric acid. Such reactions are well known in the art, and example applications to the synthesis of useful polymeric fluorosurfactants can be found in US20030109662 to Medsker, et al., and U.S. Pat. No. 6,660,828 to Thomas, both referenced above.

In one embodiment, the fluorosurfactant is present in an active weight % amount of about 0.001% to about 10%. In another embodiment, the fluorosurfactant is present in an amount of about 0.01% to about 2%. In yet another embodiment, the fluorosurfactant is present in an active weight % amount of about 0.1% to about 0.6%.

Alcohol

The alcohol used in the present invention is a lower hydrocarbon chain alcohol such as a C1-C4 alcohol. A singe alcohol or a blend of two or more alcohols may be used in the composition of the present invention. The Applicant has found that denatured alcohol may be used and in some cases preferred.

In one embodiment, the alcohol is ethanol, 2-propanol (or isopropanol), n-propanol, n-butanol, methanol and combinations thereof. In another embodiment, the alcohol is ethanol, methanol, 2-propanol and combinations thereof. In another embodiment, the alcohol is ethanol. In another embodiment, the alcohol is denatured. In yet another embodiment, the alcohol is denatured with another alcohol.

In one embodiment, the alcohol is present in an active weight % amount of about 30% to about 95%. In another embodiment, the level of alcohol is present in an active weight % amount of about 40% to about 70%. In yet another embodiment the level of alcohol is present in an active weight % amount of about 60% to about 70%.

Water

The water is present in a weight % amount of about 1% to about 70%. In yet another embodiment, the water is present in a weight % amount of about 30% to about 50%. In yet another embodiment, the water is present in a weight % amount of about 30% to about 40%.

The water to alcohol ratio in the present invention is between about 5:95 and 70:30 by weight. In another embodiment the water to alcohol ratio is about 70:30. In another embodiment, the water to alcohol ratio is about 40:60. In yet another embodiment, the water to alcohol ratio is about 30:70. In yet another embodiment, the water to alcohol ratio is about 15:85.

Detergents

Suitable detergents or surfactants include, but are not limited to, glycoside, glycols, ethylene oxide and mixed ethylene oxide/propylene oxide adducts of alkylphenols and alcohols, the ethylene oxide and mixed ethylene oxide/propylene oxide adducts of long chain alcohols or of fatty acids, mixed ethylene oxide/propylene oxide block copolymers, esters of fatty acids and hydrophilic alcohols, sorbitans, alkanolamides, soaps, alkylbenzene sulfonates, olefin sulfonates, paraffin sulfonates, propionic acid derivatives, alcohol and alcohol ether sulfates, phosphate esters, amines, amine oxides, alkyl sulfates, alkyl ether sulfates, sarcosinates, sulfoacetates, sulfosuccinates, cocoamphocarboxy glycinate, salts of higher acyl esters of isethionic acid, salts of higher acyl derivatives of taurine or methyltaurine, phenol poly ether sulfates, higher acyl derivatives of glycine and methylglycine, alkyl aryl polyether alcohols, salts of higher alkyl substituted imadazolinium dicarboxylic acids, tannics, naphthosulfonates, monochloracetics anthraflavinics, hippurics, anthranilics, naphthoics, phthalics, carboxylic acid salts, acrylic acids, phosphates, alkylamine ethoxylates, ethylenediamine alkoxylates, betaines, sulfobetaines, and imidazolines.

Detergents also include, ammonium myreth sulfate, cetamine oxide, cetyl betaine, cocamide DEA, cocamide MEA, cocamide MIPA, cocamidopropyl betainamide MEA chloride, cocamidopropyl betaine, cocamidopropyl betaine, cocamidopropyl dimethylaminohydroxypropyl hydrolyzed collagen, cocamidopropyl hydroxysultaine, cocamidopropylamine oxide, cocoamidopropylamine oxide, cocoamphocarboxyglycinate, coco-betaine, disodium cocamido MEA-sulfosuccinate, disodium cocoamphodiacetate, disodium cocoamphodipropionate, disodium laureth sulfosuccinate, disodium oleamido MEA-sulfosuccinate, disodium ricinoleamido MEA-sulfosuccinate, lauramide DEA, lauramidopropyl betaine, lauramine oxide, myristamine oxide, PEG-7 glyceryl cocoate, PEG-7 glyceryl soyate, PEG-80 glyceryl cocoate, PEG-80 glyceryl soyate, sodium C14-16 olefin sulfonate, sodium cocoamphoacetate, sodium cocoamphopropionate, sodium cocoyl apple amino acids, sodium laureth sulfate, sodium laureth sulphate, sodium lauroyl lactylate, sodium lauroyl oat amino acids, sodium lauroyl sarcosinate, sodium lauroyl wheat amino acids, sodium lauryl ether sulfate, sodium lauryl sulfoacetate, sodium lauryl sulphate, sodium trideceth sulfate, sodium trideceth sulphate, soyamidopropyl betaine, soyamidopropyl dimethylamine, stearamine oxide, TEA-dodecylbenzene sulfonate, TEA-lauryl sulfate. Additional examples of detergents include EDTA-ethylenediaminetetraacetic acid, THPEA-tetrahydroxypropyl ethylenediamine, and TEA-Triethanolamine.

In one embodiment, the detergent includes those that are skin safe. Non-limiting examples include esters of fatty acids and hydrophilic alcohols, sorbitans, alkanolamides, soaps, sarcosinates, sulfoacetates, sulfosuccinates, cocoamphocarboxy glycinate, salts of higher acyl esters of isethionic acid, salts of higher acyl derivatives of taurine or methyltaurine. In another embodiment, the detergent includes lauryl sulfate, laureth sulfate, C11 alcohol ethoxylates, cetyl stearyl alcohol ethoxylate, cocamidopropyl dimethylamine proprionate, cocamidopropyl amine oxide, and cocamidopropyl betaine. In yet another embodiment, the detergent includes EDTA, THPEA and TEA.

The level of detergent is selected to provide the desired level of activity and can be modified as desired.

Foam Boosters/Emulsifiers

Non-limiting examples of foam boosters and/or emulsifiers include sultaines, betaines, linoleamide DEA, potassium cocoate, palm kernelamide DEA, DEA-laureth sulfate, sodium myreth sulfate, potassium soyate, sodium methyl cocoyl taurate, decyl glucoside, ammonium fatty sulfosuccinate, alkanolamides, amine oxides (cetyldimethyl amine oxide), and ammonium lauryl sulfosuccinate (MONA), oleic acid, stearamide MEA, DEA-oleamide, long chain fatty alcohols, cetearyl alcohol including ceteareth-12 and ceteareth-20, cetyl alcohol, including ceteth-2 and ceteth-20, ceteareth-12, ceteareth-20, Laureth-12, Laureth-23, Polysorbate 85, Disodium Stearyl Phthalamate, acrylic copolymers, stearyl alcohol and combinations of long chain fatty alcohols and detergents, such as POLAWAX® available from Croda, Inc.

The level of foam booster and/or emulsifier is selected to provide the desired level of activity and can be modified as desired.

Emollients

Emollients are generally separated into two broad classes based on their function. The first class of emollients function by forming an occlusive barrier to prevent water evaporation from the skin surface. The second class of emollients penetrate into the skin and physically bind water to prevent evaporation. The first class of emollients is subdivided into compounds which are waxes at room temperature and compounds which are liquid oils. The second class of emollients includes those which are water soluble and are often referred to as humectants.

Non-limiting examples of emollients are short chain alkyl or aryl esters (C1-C6) of long chain straight or branched chain alkyl or alkenyl alcohols or acids (C8-C32) and their polyethoxylated derivatives; short chain alkyl or aryl esters (C1-C6) of C4-C12 diacids or diols optionally substituted in available positions by —OH; alkyl or aryl C1-C10 esters of glycerol, pentaerythritol, ethylene glycol, propylene glycol, as well as polyethoxylated derivatives of these and polyethylene glycol; C12-C22 alkyl esters or ethers of polypropylene glycol; C12-C22 alkyl esters or ethers of polypropylene glycol/polyethylene glycol copolymer; and polyether polysiloxane copolymers. Additional examples of occlusive emollients include cyclic and linear dimethicones, polydialkylsiloxanes, polyaryl/alkylsiloxanes, long chain (C8-C36) alkyl and alkenyl esters of long straight or branched chain alkyl or alkenyl alcohols or acids; long chain (C8-C36) alkyl and alkenyl amides of long straight or branched chain (C8-C36) alkyl or alkenyl amines or acids; hydrocarbons including straight and branched chain alkanes and alkenes such as squalene, squalane and mineral oil; jojoba oil polysiloxane polyalkylene copolymers, dialkoxy dimethyl polysiloxanes, short chain alkyl or aryl esters (C1-C6) of C12-C22 diacids or diols optionally substituted in available positions by OH such as diisopropyl dimer dilinoleate; and C12-C22 alkyl and alkenyl alcohols, long chain alkyl or aryl esters (C8-C36) of C12-C22 diacides or diols optionally substituted in available positions by —OH, such as diisostearyl dimer dilinoleate; lanolin and lanolin derivatives, and beeswax and its derivatives. Additional examples of emollients include Lauric Acid, Palmitic Acid, Myristic Acid, PEG-3 Glyceryl Cocoate, Propylene Glycol Diperlargonate, Octyl Stearate, Ceteth-10, Glycereth-26, Isocetyl Stearate, Octyldodecyl Stearoyl Stearate, Isopropyl Isostearate, Isostearyl Isostearate, Isostearyl Palmitate, Myristyl Stearate, Myristyl Lactate, Myristyl Myristate, Octyl Palmitate, PEG-7 Glyceryl Cocoate, Cetyl Esters, Isostearyl Neopentanoate.

In one embodiment, the emollient is glycerol, propylene glycol, dipropylene glycol, polypropylene glycol, polyethylene glycol, sorbitol, pantothenol, gluconic acid salts and dimethicone/cyclomethicone (siloxanes) and commercially available materials from Croda, under the tradename POLAWAX®.

The level of emollient is selected to provide the desired level of activity and can be modified as desired.

Antimicrobial Agents

In addition to the lower alcohols present in the composition of the present invention, other antimicrobial agents may be added. This may be particularly desirable for persistence or improved efficacy. Alternatively, the antimicrobial agent may act as a preservative. Non-limiting examples of antimicrobial agents include:

Acids: Lactic, citric, glycolic, organic/inorganic acids, gallic, hydroxy-benzoic acid; and derivatives and esters;

Alkaline Agents: Ca(OH)$_2$, NaOH, KOH;

Biguanides: Polyhexamethylene biguanide (PHMB), chlorhexidine gluconate (CHG);

Dyes: Gentian, or crystal violet, ethyl violet, brilliant green, etc., and the FD&C dyes such as Blue No. 1 and Green No. 3. In addition, other dyes include the following FD&C and D&C colors: (1) Monoazo dyes such as, but not limited to, FD&C Yellow No. 5, FD&C Yellow No. 6, (2) Diazo dyes such as, but not limited to, D&C Red No. 17, (3) Indigoid dyes such as, but not limited to, FD&C Blue No. 2, (4) Xanthene (Fluorescein) dyes such as, but not limited to, FD&C Red No. 3, (5) Anthraquinone dyes such as, but not limited to, D&C Green No. 6, (6) Quinoline dyes such as, but not limited to, D&C Yellow No. 1;

Halogens: NaOCl, Ca(OCl)$_2$, ClO$_2$;

Inorganic oxides/hydroxides: Insoluble inorganic oxides with isoelectric points greater than the pH of the solution have been shown to be efficient at the physical removal of microorganisms (bacteria and virus). Examples include magnesium hydroxide, magnesium oxide, aluminum oxide, iron oxide, cerium oxide, zinc oxide, zirconium oxide, barium oxide, calcium oxide, hydroxyapatite, chromium oxide, cobalt oxide, cesium oxide, and chrysotile asbestos;

Metals: Metal salts, which generally includes salts of metals in groups 3B-7B, 8 and 3A-5A. Specifically are the salts of aluminum, zirconium, zinc, silver, gold, copper, lanthanum, tin, mercury, bismuth, selenium, strontium, scandium, yttrium, cerium, praseodymium, neodymium, promethium, samarium, europium, gadolinium, terbium, dysprosium, holmium, erbium, thulium, ytterbium, lutetium, including silver citrate (Tinosan®);

Naturals: Also useful as antimicrobial agents are those referred to as "natural essential oils". These actives derive their names from their natural occurrence in plants. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea *origanum*, hydastis carradensis, Berberidaceae daceae, ratanhiae and *curcuma longa*. Also included in this class of natural essential oils are the key chemical components of the plant oils which include, but are not limited to, anethol, catechole, camphene, carvacol, eugenol, eucalyptol, ferulic acid, farnesol, hinokitiol, tropolone, limonene, menthol, methyl salicylate, thymol, terpineol, verbenone, berberine, ratanhiae extract, caryophyllene oxide, citronellic acid, curcumin, nerolidol and geraniol. Also useful are agents derived from naturally occurring materials, such as chitin, also known as chitosan;

Oxidants: H$_2$O$_2$, Perborate;

Phenols: Triclosan, PCMX;

Quats: Ammonium salts like benzalkonium chloride, benzethonium chloride and cetrimide; and mixtures thereof.

The level of antimicrobial agent is selected to provide the desired level of antimicrobial activity and can be modified as desired.

Other Ingredients

Additives may be added to modify the characteristics of the composition. The compositions of the present invention can comprise a wide range of optional ingredients. Non-limiting examples include, abrasives, anesthetic, colorant, fragrance, encapsulated actives, flame suppressants, flash-point suppressants, gel forming agent, indicator, insect repellant, pearlizing agent, pharmaceuticals, preservatives, skin conditioner, skin sensate, sunscreen agent, vitamins, and the like.

Methods of Preparation

The compositions of the present invention may be prepared by a variety of techniques. The order of adding the base components (i.e. fluorosurfactant, water and alcohol) will not affect the stability of the formulation. In general, the order of addition includes, mixing the water and alcohol (or other solvents) for about 10 seconds; adding the fluorosurfactant and mixing for about another 10 seconds; and finally addition of the other ingredients to optimize the formulation as needed.

Methods of Foaming and Dispensing

The present invention provides compositions formulated with a lower alcohol (C1-C4) and polymeric fluorosurfactants with pendant perfluoroalkyl side chains of a fully fluorinated chain length of C1-C7 and which can be dispensed as a foam by a trigger sprayer, pump sprayer, electrical sprayer, or the like, and may be a non-aerosol, non-aerosol self-pressurized, or aerosol-type spray means. Also suitable are other carriers, such as for example, an impregnated wipe, sponge, cloth or similar releasably absorbent or porous carrier that enables the inventive compositions to foam.

In one embodiment of the present invention, the compositions are stored and dispensed from a dispensing device that is capable of effectively transforming the liquid compositions into the physical form of a foamed composition during a dispensing operation. Benefits of dispensing and delivering the inventive compositions in the form of a foamed composition to the desired target surface include dosage control, precision in targeted delivery to a desired object or position, prevention of dripping and lost composition to unintended surfaces, such as running, pooling or dripping from a hand or vertical surface during application, decreased mobility of the dispensed compositions, decreased evaporation of active ingredients, including for example an alcoholic constituent, propellant or fragrance, as well as aesthetically pleasing characteristics of a dispensed composition in the form of a foam, including but not limited to appearance, hand-feel, perceived surface coverage of treated surfaces, creaminess, lather, and manual manipulability of the dispensed inventive compositions.

In one embodiment, the compositions are loaded onto a porous non-woven substrate in the form of a liquid composition, so that upon manipulation of the porous substrate bearing the composition, such as for example during a rigorous wiping or scrubbing motion of the non-woven substrate between the hands and fingers of a user, the physical manipulation results in the generation of a foamed composition owing to ejection of trapped air and composition from the pores of the substrate.

The compositions are particularly suited for use with dispensing devices that are capable of foaming the compositions before, during or after a dispensing operation. In one embodiment, the inventive compositions are stored in the form of a foam and dispensed in the form of a foam. In another embodiment, the inventive compositions are stored in the form of a liquid composition, and dispensed in the form of a foam.

In yet another embodiment, the inventive compositions are stored and delivered in the form of a liquid composition and foamed in situ at the site of delivery. In this embodiment, a dispensing device such as an aerosol container with a low vapor pressure solvent may be employed, such that the liquid composition is ejected to the target surface with inclusion of the low vapor pressure solvent, the latter then transforming into a vapor state and in so doing rendering the liquid inventive compositions into the form of a foam as a result of the liquid inclusions flashing into gaseous inclusions following the dispensing operation.

In another embodiment, a nozzle adapted to produce and/or maximize the inclusion of air into the ejected liquid compositions of the present invention are employed to generate a foamed composition. Many suitable nozzles are available in the art, and generally include, but are not limited to, tortuous paths, fine pin-hole orifices, fine screens and/or porous webs positioned between the liquid composition and a pressurisable portion of the dispenser capable of forcing the liquid composition through the nozzle. The turbulent flow thus produced by the various means introduce air in the form of tiny bubbles into the liquid composition during the dispensing process so as to result in the dispensing of a foamed composition. These foamable compositions deliver a stable foam which breaks on pressure application such as when a user rubs their hands or when applied over a surface. Such devices are available from the WaterGuard® Line, by Airspray®.

In an alternative embodiment, the compositions of the present invention may be formulated into an aerosol foam or mousse by addition of an appropriate propellant. The propellant must be chosen to ensure proper delivery from the container to prevent clogging of the valve. The propellant can be chosen from chlorofluorocarbons (CFCs), hydrochlorofluorocarbons (HCFCs), hydrofluorocarbons (HFCs), perfluorinated alkanes, and lower alkanes (C1-05) as well as nitrous oxide, dimethyl ether, nitrogen, carbon dioxide and solvent-soluble propellants. Preferred propellants are nitrogen, carbon dioxide and lower alkanes such as propane, butane, and isobutene.

Methods for Sanitizing the Skin

The compositions of the present invention are useful for sanitizing the skin when soap and water are not available or convenient to use. Alternatively, the compositions can be used with water.

Generally, the skin sanitizing process involves dispensing or contacting the sanitizing formulation in a hand. Spreading the sanitizer on both hands and rubbing it into the hands or applying it to another part of the body (i.e. feet). The sanitizer can be rubbed until the hands feel dry to the touch. Optionally, the sanitizer can be used with water.

The amount of the composition applied, the frequency of application and the period of use will vary widely depending upon the level of sanitization desired, e.g., the degree of microbial contamination.

Preferably, the skin sanitizing compositions of the present invention are used to sanitize human and/or animal hands and/or feet.

Treatment System (Kit)

The compositions of the present invention may be combined in the form of a treatment system (treatment kit or kit). The treatment system may further contain instructions for use of the compositions, including a list of suitable surfaces and substrates that may be treated and application techniques.

In one embodiment, the treatment system includes the inventive composition packaged in liquid form within a container having a pump dispenser means as a delivery device, optionally including instructions for proper application and use of the composition to treat or sanitize a surface, such as for example, the hands of a user. In one embodiment, instructions would include the number of dose aliquots to dispense, the desired operation in applying the composition to the hands, and contact time.

In another embodiment, instructions would be in the form of textual instructive steps, while in another embodiment, instructions would be in the form of visually recognizable pictographs representing the desired application steps in a non-verbal format. In yet another embodiment, instructions would be in the form of an audible transmitted message, such as in a digital recording, transmitted orally to the user following dispensing of the composition to provide auditory instructions as to the desired application steps. In one embodiment, the audible message would be a musical tone that persisted in time to a sufficient period to denote the desired contact time to prompt a user to continue rubbing their hands to effect complete disinfection. In yet another embodiment, instructions would be in the form a visual color change imparted to the dispensed composition, such as for example employing a disappearing colored dye system known in the art that changes the dispensed composition upon the user's hand from a first color to a second color, optionally a non-visible second color, after a particularly desirable time interval after contact with the user's hand.

EXAMPLES

The compositions and data illustrated in the Examples illustrate specific embodiments of the compositions of the present invention, but are not intended to be limiting thereof. Other modifications can be undertaken by the skilled artisan without departing from the spirit and scope of this invention All exemplified compositions can be prepared by conventional formulation and mixing techniques. Component amounts are listed as amounts listed in percentage ("%'s") are in weight percent (based on 100% active) of the composition alone and exclude minor materials such as fillers, etc., typically used to modify the compositions characteristics.

Exemplary compositions are listed in Table 1. They were prepared as described above and foamed using a pump foamer from the WaterGuard® line, by Airspray®, code number WRT4. WRT4 has three different outputs ranging from 0.75 to 1.50 ml. The foam quality was then evaluated on a scale of 1 to 10, 1 meaning no foam and 10 meaning a mousse type foam.

TABLE 1

Compositions of the Invention

| INGREDIENT | WEIGHT % | FOAM QUALITY |
|---|---|---|
| Composition 1 | | |
| PolyFox 156A | 0.6% | 1 |
| Water | 98% | |
| Composition 2 | | |
| Alcohol B | 65% | 0 |
| Water | 35% | |
| Composition 3 | | |
| PolyFox 156A | 0.6% | 1 |
| Alcohol A | 65% | |
| Water | 33% | |
| Composition 4 | | |
| PolyFox 156A | 0.6% | 5.5 |
| Alcohol B | 30% | |
| Water | 68% | |
| Composition 5 | | |
| PolyFox 156A | 0.6% | 6 |
| Alcohol B | 40% | |
| Water | 58% | |
| Composition 6 | | |
| PolyFox 156A | 0.6% | 5 |
| Alcohol B | 65% | |
| Water | 33% | |
| Composition 7 | | |
| PolyFox 156A | 0.6% | 5 |
| Alcohol B | 70% | |
| Water | 28% | |
| Composition 8 | | |
| PolyFox 156A | 2% | 2 |
| Alcohol B | 65% | |
| Chitosan | 2% | |
| Water | 31% | |

TABLE 1-continued

Compositions of the Invention

| INGREDIENT | WEIGHT % | FOAM QUALITY |
|---|---|---|
| Composition 9 | | |
| PolyFox 156A | 0.6% | 2 |
| Alcohol C | 65% | |
| Water | 33% | |
| Composition 10 | | |
| PolyFox 156A | 0.6% | 2-4 |
| Alcohol D | 65% | |
| Water | 33% | |
| Composition 11 | | |
| PolyFox 156A | 0.6% | 0 |
| Alcohol E | 65% | |
| Water | 33% | |
| Composition 12 | | |
| PolyFox 156A | 0.6% | 5.5 |
| Alcohol F | 65% | |
| Water | 33% | |
| Composition 13 | | |
| PolyFox 156A | 0.6% | 5 |
| Alcohol B | 62% | |
| Alcohol F | 3% | |
| Water | 33% | |
| Composition 14 | | |
| PolyFox 156A (rapid collapse) | 0.6% | 5 |
| Alcohol C | 67.7% | |
| Tinosan ® | 0.3% | |
| Water | 25.2% | |
| Composition 15 | | |
| PolyFox 151N | 0.85% | 5 |
| PolyFox 156A | 1.2% | |
| Alcohol D | 50% | |
| Water | 42.3% | |

Chemical Key:
PolyFox 156A = 30% active by weight; anionic salt of fluoropolyether disulfate, $R_f = C_2F_5$, available from Omnova Solutions, Inc. Av. MW = 1800 g/mole, $Q_f = 2.0$.
PolyFox 151N = 50% active by weight = nonionic polyethylene oxide block fluorinated polyether, $R_f = C_2F_5$, available from Omnova Solutions, Inc. with a diol functionality $Q_f = 2.0$
Alcohol A = 100% ethanol available from Gold Shield.
Alcohol B = Ethyl alcohol 85%, Isopropyl alcohol 6.4%, water 5.0%, Methyl alcohol 2.9%, Methyl isobutyl ketone 0.7%, available from Fisher Scientific.
Alcohol C = (SDA-3C) Ethyl alcohol 95.38% and isopropyl alcohol 4.62%
Alcohol D = (SDA-40B) Ethyl alcohol 95%, Tert-butyl alcohol 0.125%, Denatonium benzoate (Bitrex brand) 0.000488%, water 4.8745% available from Archer Daniels Midland Company.
Alcohol E = 100% Isopropanol alcohol
Alcohol F = 100% methanol
Chitosan = 99% laboratory grade chitosan; 1% citric acid, available from Sigma Aldrich
Tinosan ® = Tinosan ® SDC (20% citric acid; 0.24% silver) available from Ciba Specialty Chemicals

We claim:

1. A foamable alcohol composition comprising:
   (a) 30-95% by active weight $C_1$-$C_4$ alcohol, or mixtures thereof;
   (b) 0.001-10% by active weight polymeric fluorosurfactant, wherein the fluorosurfactant is according to structure II:

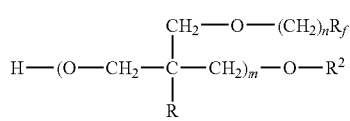

m>about 1 to about 100;
   n is about 1 to about 50;
   k is about 1 to about 50; including n=k;

$R_f$ and $R_g$ are independently selected from the group consisting of: —$CF_3$, —$CF_2CF_3$, —$(CF_2)_pCF_3$, —$R'CF_3$, —$R'(CF_3)_p$, —$R''(CF_3)_q$, perfluorinated alkyl radical, perfluorinated aryl radical, partially fluorinated alkyl radical, partially fluorinated aryl radical, derivatives thereof, and combinations thereof;
   R' is a $C_1$ to $C_{20}$ linear or branched, alkyl or alkylene moiety, optionally substituted with and/or terminated with at least one —$CF_3$ group;
   R" is a radical comprising a phenyl, aryl group and combinations thereof with q degrees of —$CF_3$ substitution;
   p is about 1 to about 6;
   q is about 1 to about 5;
   R is hydrogen, or —$CH_2O(CH_2)_kR_g$ or an alkyl comprising from about 1 to about 6 carbon atoms;
   $R^2$ is an alkyl having from about 1 to about 40 carbon atoms;
      wherein R and $R^2$ may be alkyl, alkylene moieties derivatized with radicals comprising carboxylic, ester, amine, amide, aminoamide, siloxane, silyl, alkylsiloxane, perfluoroalkyl and combinations thereof;
   (c) 1-70% water; and
   wherein the composition is capable of being foamed.

2. The composition according to claim 1, wherein p is about 1 to about 4.

3. The composition according to claim 1, wherein p is about 1 to about 2.

4. The composition according to claim 1, wherein the polymeric fluorosurfactant is selected from molecules corresponding to structure II further comprising, derivatives of the structure II, wherein derivation at $R^2$ is independently performed by covalent attachment of:
   (c) polar nonionic groups, selected from the group consisting of poly(alkylene oxide), poly(ethylene oxide), polypropylene oxide), polyether copolymers, carbonyl, nitrile, thiol, cyano groups, and combinations thereof.

5. The composition according to claim 4, wherein the nonionic group is poly(ethylene oxide).

6. The composition according to claim 1, wherein the alcohol is selected from the group consisting of ethanol, methanol, 2-propanol, and mixtures thereof.

7. The composition according to claim 1, wherein the alcohol is ethanol.

8. The composition according to claim 1, wherein the fluorosurfactant is about 0.01% to about 2% by active weight.

9. The composition according to claim 1, wherein the alcohol is about 40% to about 85% by active weight.

10. The composition according to claim 1, wherein the alcohol is about 60% to about 70% by active weight.

11. The composition of claim 1, wherein the composition is mixed with air to form the foam and the foam is dispensed in a fixed dose amount.

12. The composition according to claim 1, wherein the composition is capable of instantly sanitizing a surface.

13. A skin sanitizing composition comprising:
   (a) 30-95% by weight $C_1$-$C_4$ alcohol, or mixtures thereof;
   (b) 0.001-10% by weight polymeric fluorosurfactant, wherein the fluorosurfactant has a pendant side chain of C1-C7 and wherein the polymeric fluorosurfactant has is according to structure II:

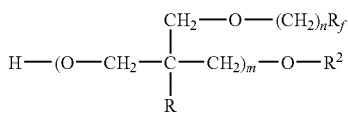

wherein n is about 1 to about 50;
m>about 1 to about 100;
$R_f$ and $R_g$ are independently selected from the group consisting of: —$CF_3$, —$CF_2CF_3$, —$(CF_2)_pCF_3$, —$R'CF_3$, —$R'(CF3)_p$, $R''(CF_3)_q$, perfluorinated alkyl radical, perfluorinated aryl radical, partially fluorinated alkyl radical, partially fluorinated aryl radical, derivatives thereof, and combinations thereof;
p is about 1 to about 6;
q is about 1 to about 5;
R' is a $C_1$ to $C_{20}$ linear or branched, alkyl or alkylene moiety, optionally substituted with and/or terminated with at least one —$CF_3$ group;
R" is a radical comprising a phenyl, aryl group and combinations thereof with q degrees of —$CF_3$ substitution;
p is about 1 to about 6;
q is about 1 to about 5;
R is hydrogen, or —$CH_2O(CH_2)_kR_g$ or an alkyl comprising from about 1 to about 6 carbon atoms; k is about 1 to about 50; including n=k;

$R^2$ is an alkyl having from about 1 to about 40 carbon atoms;
wherein R and $R^2$ may be alkyl, alkylene moieties derivatized with radicals comprising carboxylic, ester, amine, amide, aminoamide, siloxane, silyl, alkylsiloxane, perfluoroalkyl and combinations thereof;
(c) water to balance the composition; and
wherein the composition is capable of being foamed and sanitizing the skin, optionally including an antimicrobial agent other than alcohol.

14. The skin sanitizing composition according to claim 13, wherein the antimicrobial agent is selected from the group consisting of chitosan, silver citrate, quaternary ammonium halides, triclosan, phenols and derivatives, hydrogen peroxide, lactic acid, citric acid, glycolic acid and mixtures thereof.

15. The skin sanitizing composition according to claim 13, wherein the fluorosurfactant is not known to bioaccumulate.

16. A delivery system for treating a surface, wherein the system comprises:
(a) a composition of claim 1; and
(b) a dispensing device capable of delivering the composition to the surface in the form of a foamed composition, said dispensing device selected from the group consisting of an aerosol or non-aerosol, trigger sprayer or pump sprayer, and combinations thereof.

* * * * *